United States Patent [19]

Cuffe et al.

[11] Patent Number: 5,287,291
[45] Date of Patent: Feb. 15, 1994

[54] QUIET BUS FOR THE BUSING OF ANALOG AND DIGITAL DATA

[75] Inventors: John W. Cuffe, State College; Alan D. Weiner, New Bloomfield, both of Pa.

[73] Assignee: Krautkramer-Branson, Incorporated, Lewistown, Pa.

[21] Appl. No.: 753,816

[22] Filed: Sep. 3, 1991

[51] Int. Cl.$^5$ .................. G06F 15/20; G01N 29/18
[52] U.S. Cl. ....................... 364/507; 73/598; 395/325
[58] Field of Search ........... 364/506, 508; 73/598; 395/200, 275, 325

[56] References Cited

U.S. PATENT DOCUMENTS

| | | | |
|---|---|---|---|
| Re. 30,926 | 5/1982 | Ross et al. | 73/638 |
| 3,942,361 | 3/1976 | Rath et al. | 73/624 |
| 4,102,205 | 7/1978 | Pies et al. | 73/626 |
| 4,129,041 | 12/1978 | Bicke | 73/657 |
| 4,169,662 | 10/1979 | Kaule et al. | 359/285 |
| 4,289,033 | 9/1981 | Prause et al. | 73/622 |
| 4,333,346 | 6/1982 | Renzel | 73/606 |
| 4,373,394 | 2/1983 | Renzel et al. | 73/606 |
| 4,432,235 | 2/1984 | Renzel et al. | 73/611 |
| 4,437,332 | 3/1984 | Pittaro | 73/1 DV |
| 4,821,575 | 4/1989 | Fujikake et al. | 73/626 |
| 4,947,351 | 8/1990 | Moran et al. | 364/508 |

Primary Examiner—Thomas G. Black
Assistant Examiner—Michael Zanelli
Attorney, Agent, or Firm—Polster, Lieder, Woodruff & Lucchesi

[57] ABSTRACT

Test apparatus (10) performs non-destructive testing of an object (O) to determine if it has flaws or defects. An ultrasonic wave (W) is generated and directed at the object. A return wave (R) reflected by the object is received and analyzed to determine if a flaw or defect. The return wave is converted to digital data which is stored for purposes of later analysis. For this purpose, digital signals containing the data are routed over a quiet bus (24). Digital signals are routed over the bus prior to generation of an ultrasonic wave to establish test parameters. Digital noise may occur during the transmission. A controller (22) controls routing of digital signals over the bus. The controller inhibits the flow of digital signals over the bus during that portion of an operational cycle of the apparatus during which the ultrasonic waves are produced and return waves evaluated. The controller allows transmission of digital signals over the bus at other times. As a result, the ultrasonic portion of the apparatus is effectively isolated from the bus so any digital noise thereon cannot effect the ultrasonic portion of the apparatus and the test results produced thereby.

15 Claims, 3 Drawing Sheets

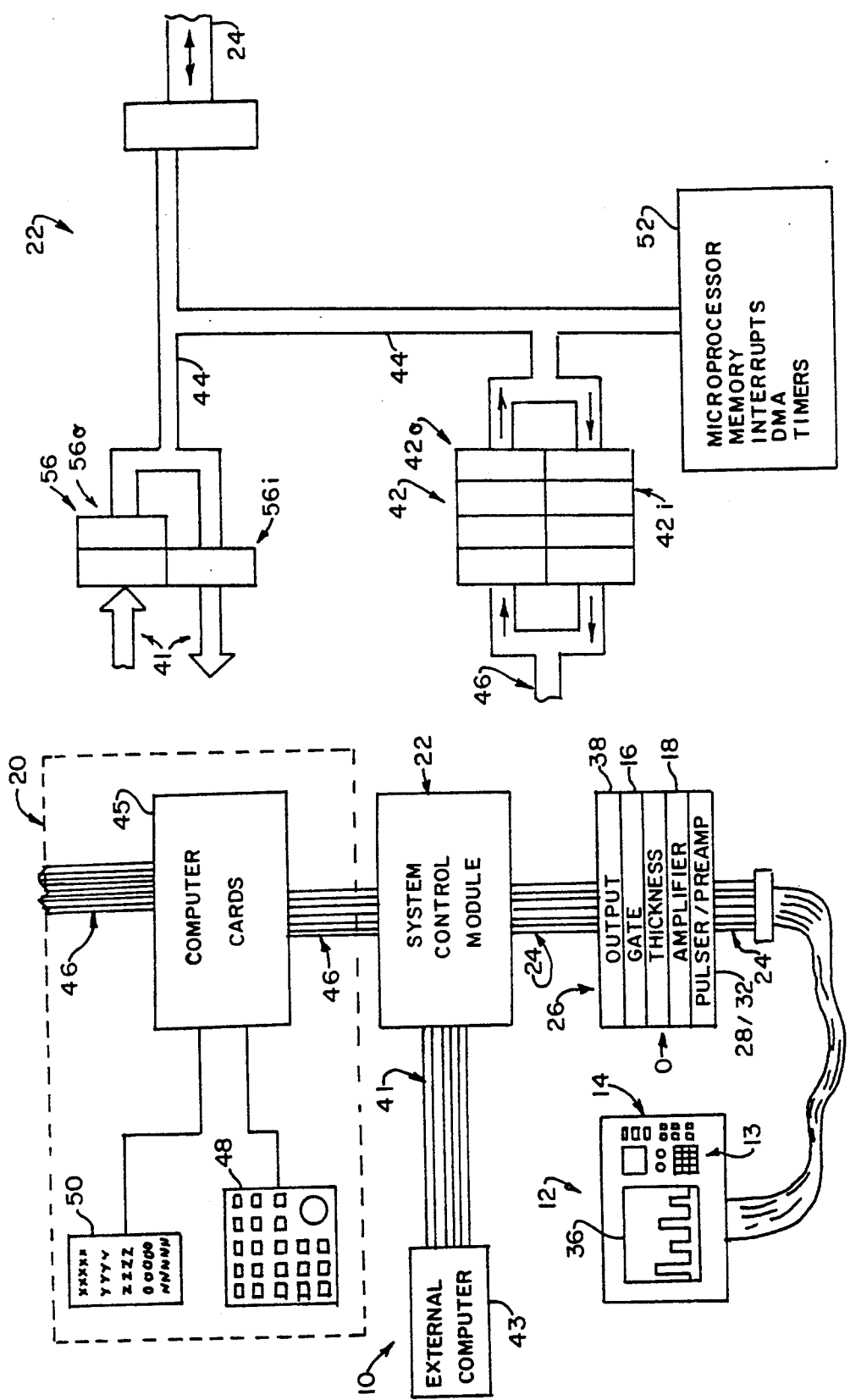

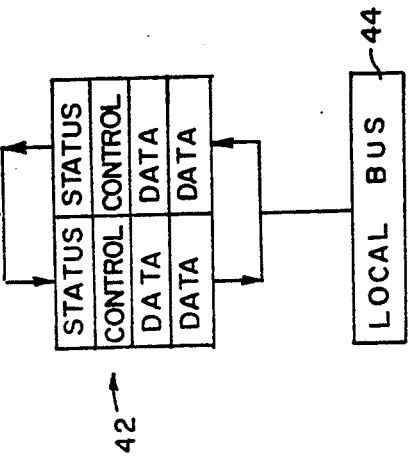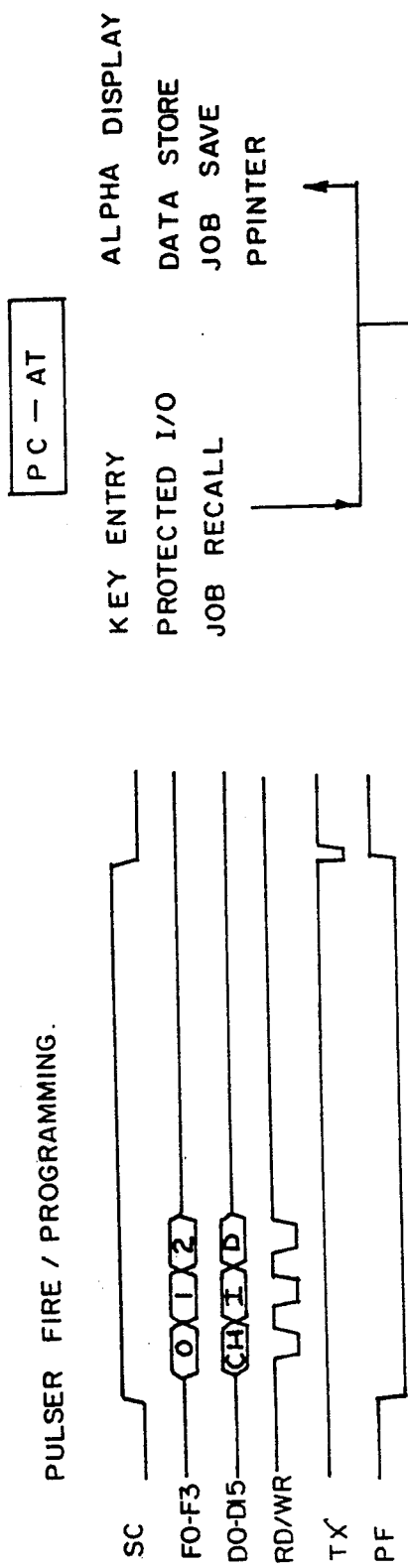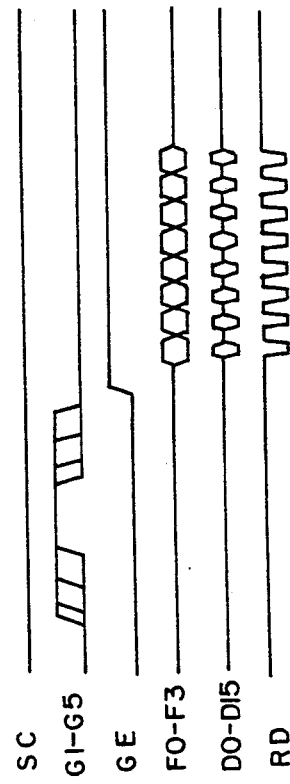

QUIET BUS FOR THE BUSING OF ANALOG AND DIGITAL DATA

BACKGROUND OF THE INVENTION

This invention relates to testing apparatus such as ultrasonic flaw detectors having both analog and digital signals present in various parts thereof and, more particularly, to such apparatus in which noise present in the digital portion of the apparatus is prevented from corrupting the analog signals and thereby invalidating a test involving the apparatus.

Ultrasonic testers for the non-destructive testing of objects are well known in the art. In operation, ultrasonic waves are generated by appropriate transducers and directed at an object under test Depending upon the test being performed, the wave may pass through the object, or strike its surface and be reflected back. The resultant return wave is converted to an analog signal whose characteristics (amplitude, for example) are indicative of the structure of the object. There are various applications for testing apparatus such as ultrasonic wave testers. Representative test applications are shown in U.S. Pat. Nos. 4,821,575, 4,437,332, 4,432,235, 4,373,394, 4,333,346, 4,289,033, 4,169,662, 4,129,041, and 4,102,205, all of Which are assigned to the same assignee as the present application.

As indicated in various of these patents, microprocessors are used with the testing apparatus. More recently, personal computers (PC's) have also been employed with the apparatus. A particular advantage with using PC's is that they are easily programmed to allow a wide range of post testing data analysis. For this purpose, the return information is converted to digital data which are stored for later retrieval and analysis. Prior to the start of a test, digital information is sent over the bus to configure the test apparatus for a chosen set of test parameters. The digital data is routed over a digital bus to a storage site. As is typical, the frequency of digital information transmitted over the bus is in the range of 5 Mhz-10 Mhz. These frequencies, however, correspond to those of the ultrasonic transducers within the apparatus. Digital noise which is present on the bus is picked up by amplifiers within the ultrasonic portion of the apparatus. Because of the overlapping frequencies, the amplified digital noise is integrated with the ultrasonic signals, thus distorting this latter signal and the information it contains about the object. The resultant distortion can, effectively, invalidate the test. It is therefore important, not only for ultrasonic wave testing, but also for similar test configurations where analog and digital signals are present, to prevent the noise present on the digital side of the apparatus from adversely effecting the analog signals.

SUMMARY OF THE INVENTION

Among the several objects of the present invention may be noted the provision of test apparatus for performing non-destructive tests on an object or workpiece to determine if it has defects or flaws; the provision of such test apparatus to utilize both analog and digital data signals for real-time test indications and post-test data analysis; the provision of such test apparatus with which a personal computer or microprocessor is used for control of testing, data storage, retrieval, and analysis; the provision of such test apparatus having a controlled data bus over which digital information can flow only during certain periods, and, in particular, only during those periods when no analog data signals are present thereby to prevent digital noise from distorting the analog signals and invalidating test results; the provision of such apparatus to be ultrasonic wave testing apparatus; the provision of such ultrasonic wave testing apparatus which is useful in a wide variety of testing applications; and, the provision of a method for ultrasonic, non-destructive testing of an object employing the apparatus.

In accordance with the invention, generally stated, testing apparatus performs non-destructive testing of an object to determine if it has flaws or defects An ultrasonic wave portion of the apparatus periodically generates an ultrasonic wave which is directed at the object. A return wave reflected by the object is received and analyzed to ascertain the condition of the object. An electronic portion of the apparatus produces digital data signals which are stored in an appropriate memory for later recall and post test evaluation and analysis. The digital data is transmitted to the memory over a data bus. This bus is subject to the presence of digital noise as data signals are routed thereover. A controller which controls movement of electrical signals over the bus inhibits flow of electrical signals thereover during that portion of an operational cycle during which the ultrasonic portion of the apparatus is functioning. The controller allows transmission of electrical signals over the bus during that part of the cycle when the ultrasonic portion is not generating and transmitting waves. This controller acts to isolate the two portions of the apparatus from each other for the digital noise which might otherwise effect operation of the ultrasonic portion of the apparatus to not do so.

As a method, the invention includes generating an ultrasonic wave, directing the wave at the object, receiving a return wave reflected by the object, and evaluating the return wave to determine the condition of the object. The method further includes producing digital data signals and storing the data for analysis. Storing the data includes routing the data signals over a bus. To prevent noise present on the data bus from effecting the evaluation of the ultrasonic waves includes control of the routing of data signals over the bus. The movement of data signals over the bus is inhibited during that portion of a test cycle during which ultrasonic waves are generated and evaluated, and allowed during that portion when the wave is not being generated. As a result, the ultrasonic wave processing is effectively isolated from any noise so the results of the evaluation are not effected. Other objects and features will be in part apparent and in part pointed out hereinafter.

BRIEF DESCRIPTION OF THE DRAWINGS

FIG. 2 is a block diagram of the apparatus of the present invention;

FIG. 3 is a block diagram of a system control module of the apparatus;

FIG. 4 is a block diagram of the interface between a quiet bus and a personal computer used therewith; and, FIGS. 5A and 5B are timing diagrams for the transfer of digital data over the quiet bus.

Corresponding reference characters indicate corresponding parts throughout the drawings.

DESCRIPTION OF A PREFERRED EMBODIMENT

Figure 1A:
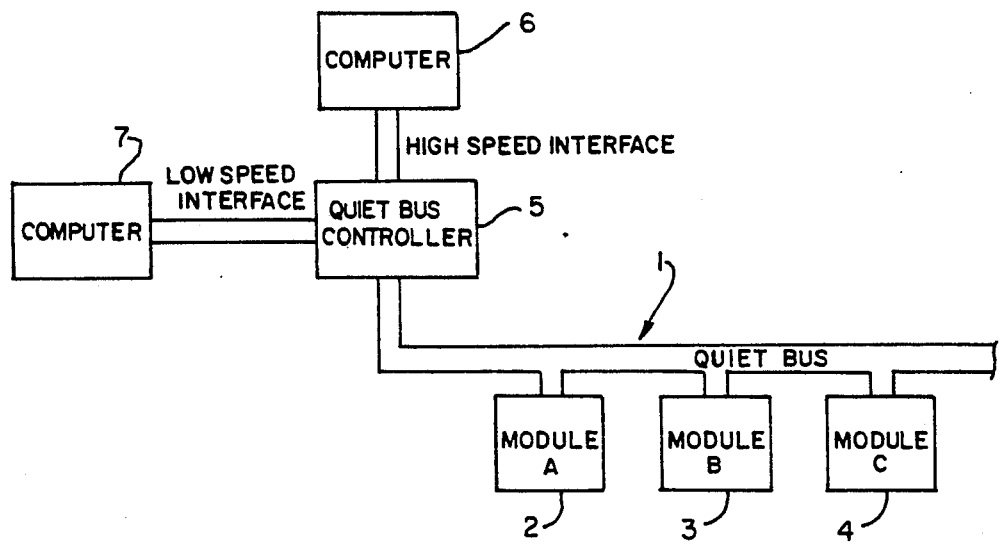
FIG. 1A is a block diagram of a quiet bus of the present invention.

Referring to the drawings, a quiet bus of the present invention is indicated generally 1 in FIG. 1A. The quiet bus is for use in transferring both analog and digital signals between various modules 2, 3, and 4.

Routing of these signals is controlled by a quiet bus controller 5. As will be described in more detail hereinafter, the modules contain digitally controlled parameters which are utilized to establish a particular test configuration. During performance of the test, the modules process and generate analog data. Finally, at the completion of the test, the modules generate digital data which can be stored for later retrieval and analysis. During a test sequence, both analog and digital signals move over quiet bus 1.

In addition to the foregoing, the bus controller interfaces with respective computers 6 and 7. Computer 6 has a high speed interface with controller 5 to enable real-time changes in the test parameters, based on processed analog data, to be made. Computer 7 has a low speed interface with the controller. This latter computer acts as an intermediary between bus 1 and an operator of a system in which the bus is employed. The computer allows the user to change parameters or view processed data at a human rate.

Because of the operations which can be performed using the quiet bus, the possibility exists that both digital and analog signals exist on bus 1 at the same time. Moreover, digital noise associated with the digital signals can be introduced into amplifiers (not shown) contained within modules 2, 3, and 4. Because these amplifiers will amplify signals in the bandwidth at which the digital noise occurs, this noise is amplified. If the noise occurs at the same time an analog signal is being generated or processed within the module, the noise can alter the characteristics of the analog signal and distort the information it represents. Such occurrence can invalidate the results of the test being performed.

To prevent this, controller 5 operates to breakdown signal transfer over the quiet bus into three distinct segments during any test cycle. In the first segment, digital signals are allowed on the bus to the modules to configure the modules with the parameters for the test being performed. No analog signals are routed over the bus at this time. During the second segment, analog signals are moved over the bus for test purposes. No digital signals are allowed on the bus during this segment. Lastly, digital signals are again allowed on the bus, and analog signals inhibited from moving thereover. Now, instead of setting test parameters, the digital signals convey data to be stored for later retrieval.

By establishing a quiet bus and using it by the method described, digital noise, if it occurs, has no effect on performance of the test, or its results. What follows is the description of apparatus for practically using the bus.

Figure 1B:
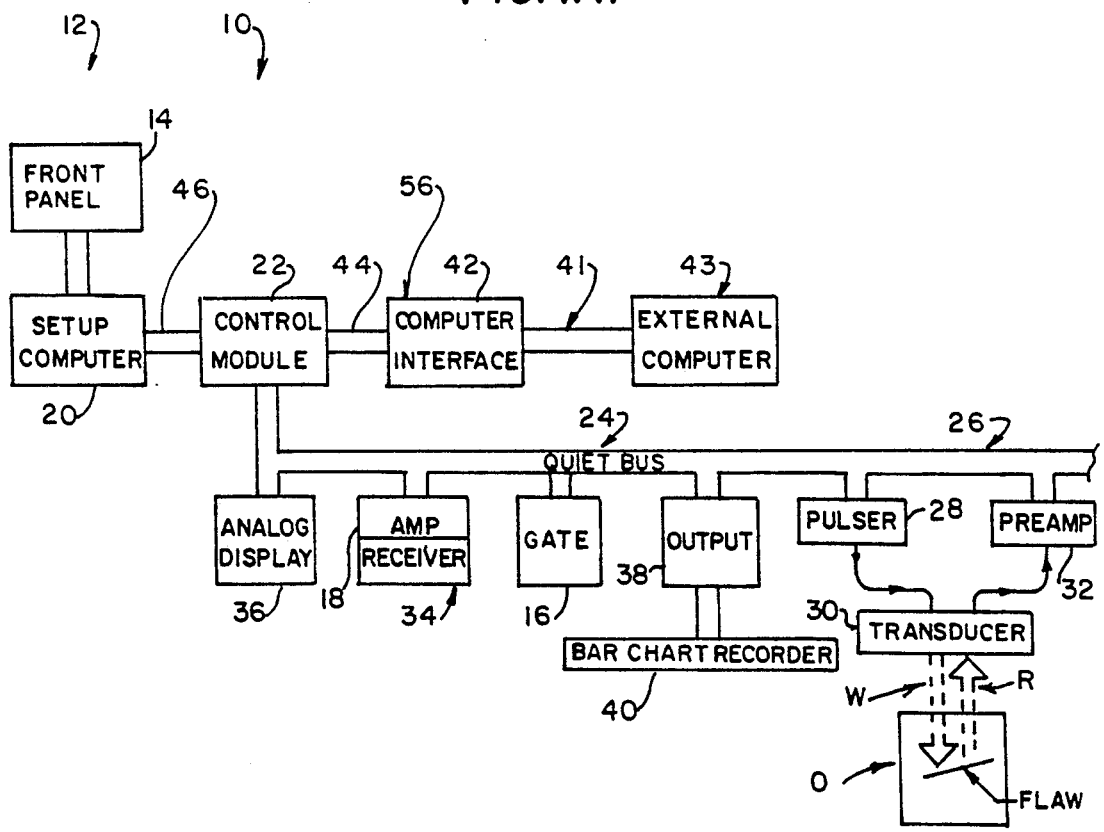
FIG. 1B is a block diagram illustrating how a non-destructive test using ultrasonic waves is performed.

Referring now to FIG. 1B, apparatus for conducting a non-destructive test of an object 0 to determine whether or not the object has a flaw or defect is indicated generally 10 in FIG. 1B. Apparatus 10 employs a pulse-echo ultrasonic pulse technique such as is well-known in the art. Various testing arrangements with which apparatus 10 may be usable include testing of specimens such as tubes and rods, and thick walled objects. Testing of these objects is discussed, for example, in U.S. Pat. Nos. 3,942,361, and 4,289,033 which are assigned to the same assignee as the present application. Those skilled in the art will be aware of other testing arrangements also.

Apparatus 10 includes a flaw detector 12 such as that commercially available from the Krautkramer Branson Corporation of Lewiston, Pa., under their model designation USIP 20. Depending upon the test being performed, a user makes various settings using controls 13 on the front panel 14 of the instrument. These settings include, for example, the number of flaw gates 16 (see FIG. 2) involved, threshold levels, the gain levels of amplifiers 18 (again, see FIG. 2), etc. The instrument settings are stored in a set-up computer 20 and are transferred from there to a control module or controller 22 within the instrument.

At the start of a test, a system clock signal $S_c$ (see FIG. 5A) is transmitted over a quiet bus 24 to an ultrasonic portion 26 of the apparatus. Bus 24 is designed for bi-directional flow of electrical signals, these being both digital and analog signals. A pulser 28 is interposed between the bus and a transducer 30, and a pulser fire signal $P_f$ is transmitted simultaneously with the clock signal. At the end of this latter signal, the pulser is fired. The transducer is responsive to the firing of the pulser to generate an ultrasonic wave W which is directed at the object O under test.

The duration of the system clock signal marks the first segment of a test cycle. During this segment controller 22 only allows digital signals on the quiet bus. The digital information during this segment contains, at a minimum, a channel number (there are up to 256 channels) to evaluate. The digital information may also contain test programming or parameter reading information. The bus includes sixteen (16) data lines $D_o$-$D_{15}$, four (4) function lines $F_o$-$F_3$, and read/write lines. The type of information on the bus is determined by binary state of the function lines. For example, if all the function lines are set to 0, i.e. $F_o$-$F_e$ are 0,0,0,0, the information on the data lines designate the number of the channel to be evaluated. If, for example, the function lines are 0,0,0,1 then the data lines convey current parameter address information. As a further example, if the function lines are 0,0,1,0 data for a parameter address is set or gotten. FIG. 5A represents a typical set-up cycle in which one parameter is being modified. Finally, when, for example, the function lines are 0,1,0,1 read signal on the bus will cause processed data generated at a gate module to be obtained.

At the end of the system clock signal, the controller inhibits flow of digital signals over the quiet bus and allows analog signals to move thereover. This period coincides with the firing of the pulser 28 and the generation and transmission of the ultrasonic wave. A return wave R, which is reflected back from the object is received by transducer 30 and converted back to an electrical signal. This conditioned signal, which is an analog signal, is amplified by a preamplifier 32 and routed over the quiet bus to a receiver 34 which includes the amplifier 18. The receiver conditions the signal. The resultant output from the receiver is supplied both to the gate 16 and to an analog display 36 over the quiet bus. The analog display is, for example, on the front panel of the instrument. As shown in FIG. 5B, gate signals $G_1$-$G_5$ are supplied by the gates. After the last gate has ended, a gate ended signal $G_e$ is supplied over the bus to indicate the ultrasonic (analog) portion of the test is over. The function line signals $F_0$-$F_3$, and data line signals $D_0$-$D_{15}$ are now applied to the quiet bus to read in the data generated by the test. Additionally, a data output module 38 may capture the data from the quiet bus and convert it for output as, for example, to a bar chart recorder 40.

The above sequence of operations outlines the operation of the apparatus with respect to the generation of ultrasonic waves and the subsequent conversion of these waves to analog electrical signals which are then processed to obtain real-time information about the object under test. It will be understood that the apparatus is a multi-channel apparatus. For example, instrument 12 can be configured for up to 256 channels of operation so that many transducers can be directed at the object to obtain information concerning flaws or defects.

Referring to FIGS. 2 and 3, with the advancements in computers and related software technology, it is now possible for a user of the apparatus to extract real-time analog data from a test, convert it to digital data, store the digital data and retrieve it at a later time for further analysis. In addition, the user is now also able to modify test parameters real-time, so to effectively dynamically reconfigure the test apparatus as a test is being done.

It will be understood that for a 256 channel instrument such as detector 12, there are numerous parameters. This is true even for a single channel instrument. Thus, detector 12 includes an internal computer 20 having a keypad 48 and alpha-numeric display or monitor 50. This internal computer interfaces with system control module 22 via, for example, an IBM PC AT bus 46. This internal computer is able to extract the data from a test at high rates of speed but otherwise the interface with the controller is at much lower rates, for example, 30 Hz.

An external computer 43 is connectable to the detector via a high speed interface 56 and an associated bus 41. Computer 43 communicates with the system controller at the same speed at which the controller operates the quiet bus. This is the ultrasonic repetition rate of up to 10 KHz. Consequently, the user has the capability to modify test parameters real-time, together with a data extraction capability. The high speed interface 56 is available from Krautkramer Branson under its model designation 7610.

Referring to FIG. 4, PC 20 is shown to enable the user to perform the functions noted above. By entering appropriate instructional commands using the keypad, the user directs data to be stored, has it recalled, displayed on a monitor, printed out, or saved to a disk or other data storage medium. In the display, the user can manipulate the data so it is presented in forms different than that in which it can be displayed in real time.

Referring again to FIG. 3, control module 22 includes a microprocessor 52 which is responsive to the instrument settings to control both the ultrasonic (analog) portion of the operational cycle, and the digital portion thereof. As noted, module 42 serves as an intermediary between the internal computer and the control computer. This allows internal computer 20 to interact with computer 52 at a low rate while the control computer interacts with quiet bus 24 at a much higher rate. The microprocessor includes memory, timing, interrupt, and direct memory access (DMA) functions. The microprocessor controls signal routing over the quiet bus, as, for example, at the start of a test cycle when it generates the system clock signal and channel number. For digital data storage, a high speed control and interface module 56 is connected to local bus 44 and has both input and output registers 56I and 56O respectively. The transmissions back and forth between the internal computer 20 and the control module, and between the control module and external computer 43 are always through one set of input/output registers or the other. There are no direct connections between the control module and either of the other elements.

It is, as noted, a feature of the present invention that digital data signals are not routed over the quiet bus during the operation of the ultrasonic portion of the apparatus. This is because the frequency of information routed over quiet bus 24 is in the same range (5 Mhz–10 Mhz), which corresponds to that of the frequencies generated by ultrasonic transducers 30. When digital data is moved via the quiet bus, digital noise which may occur on the bus would be picked up by the amplifiers 18. Because of the amount of amplification provided by the amplifiers, the amplitude of any digital noise is greatly magnified. Further, this digital noise is amplified together with the analog signals representing the received ultrasonic data from the test. As a result, the analog information is distorted by the digital noise and incorrect test results are obtained. In consequence, the test results could be invalid.

To prevent this, the control module inhibits any digital data transfer over bus 24 simultaneous with the operation of ultrasonic portion 26 of the apparatus. Since no digital signals are moving on the bus as the analog signals are routed thereover, no digital noise is present to distort the analog signals. At the end of the ultrasonic portion of a test cycle, the apparatus enters a data transfer portion. Although digital noise may be present on the bus, there are no analog signals which it could effect. Once the data has been stored, the interface between the computer and the instrument can be broken. Now, the stored data can be directly recalled for analytical purposes. And, the user can work with the data knowing that it truly reflects the results of the test.

What has been described is a quiet bus and its use in a testing arrangement which permits non-destructive testing of an object with real-time data presentation capability. This, together with the ability to convert the test data from an analog to a digital format and store the digital data for later analysis. Further, the test apparatus interfaces with both an internal and an external computer. This allows for the storage of digital data, as well as operation at real-time control of a test, and later work with the data for purposes of analysis. Importantly, the quiet bus allows the test apparatus to have a control capability which insures the quality of both the real-time analog information and the digital data. The controller accomplishes this by controlling operation of the quiet bus over which data of both types is routed. The controller manages data flow so that digital data, and, more importantly, associated digital noise, is not present on the quiet bus at the same time as any analog data. Consequently, even though amplifiers for magnifying the analog signal would, because of the frequencies at which digital noise occurs, amplify the noise and analog signals together, thus distorting the analog signals and effecting the integrity of the test, this does not occur since digital and analog signals are never allowed on the quiet bus at the same time.

In view of the foregoing, it will be seen that the several objects of the invention are achieved and other advantageous results are obtained.

As various changes could be made in the above constructions without departing from the scope of the invention, it is intended that all matter contained in the above description or shown in the accompanying drawings shall be interpreted as illustrative and not in a limiting sense.

Having thus described the invention, what is claimed and desired to be secured by Letters Patent is:

1. Testing apparatus for performing non-destructive testing of an object to determine if it has flaws or defects comprising:

wave means for generating an ultrasonic wave, for directing the wave at the object, for receiving a return wave reflected by the object, and for analyzing the return wave to determine if a flaw or defect is present in the object;

means for converting the return wave to a digital data signal for analysis;

bus means over which the digital data signal is routed, and, control means for controlling the routing of digital data signals over the bus means, the control means inhibiting flow of digital signals over the bus means during that portion of an operational cycle of the apparatus during which the wave means is operating, and allowing transmission of digital signals over the bus means when the wave means is not operating, wherein the ultrasonic portion of the apparatus is effectively isolated from the bus means to prevent digital noise from effecting test information developed by the ultrasonic portion.

2. The apparatus of claim 1 further including internal computer means for controlling testing parameters and for storing the digital data signals for later analysis, the internal computer means interfacing with the control means.

3. The apparatus of claim 2 further including external computer means, interfacing with the control means for manipulating test parameters and acquiring test data at a rate different from that at which the internal computer means acts.

4. The apparatus of claim 3 further including input-/output register means at the respective interfaces between the respective computer means and the control means thereby to isolate the quiet bus from each.

5. In an ultrasonic flaw detector apparatus having an ultrasonic section in which ultrasonic waves are periodically generated and directed at a part under test, and return waves are received and evaluated to determine the existence of flaws or defects in the part, the improvement comprising:

means for converting the information contained in the return waves to digital data signals;

computing means for setting test parameters and for storing said digital data for subsequent evaluation and analysis;

bus means over which said digital data is routed to the storage means, said bus means being subject to the presence of digital noise when said digital data is being routed thereover; and, bus controller means for controlling operation of the bus to co-ordinate routing of said digital data thereover with operation of the ultrasonic section of the apparatus, said controller means inhibiting flow of said digital data over the bus means during the period when the ultrasonic section is operating, and allowing flow of digital data thereover when the ultrasonic section is not operating, thereby to prevent digital noise from effecting test information developed by the ultrasonic section.

6. The improvement of claim 5 further including interface means for interfacing the computing means with the bus controller means, the interfacing means isolating the bus means from the computing means.

7. A quiet bus for routing both analog and digital data signals from one location in a system to another, the bus interfacing with control means which controls the flow of analog and digital signals thereover with the analog signals being routed between one set of locations within the system and the digital signals between a different set of locations therewithin, and the control means controlling flow of analog and digital signals such that the analog and digital signals are not simultaneously present on the bus wherein digital noise associated with the presence of the digital signals cannot effect the signal characteristics of the analog signals.

8. The quiet bus of claim 7 further in which the system interfaces with computing means for storing digital data and for using the data for analytical purposes.

9. The quiet bus of claim 8 for use in a system for ultrasonically testing an object to detect flaws or defects therein.

10. A method of performing non-destructive testing of an object to determine if it has flaws or defects comprising:

generating an ultrasonic wave, directing it at the object, receiving a return wave from the object, and analyzing the return wave to determine if a flaw or defect is present in the object;

converting the return wave to a digital data signal and storing the data represented by the digital signal;

routing the digital signal over bus means for storing the data; and, controlling the routing of digital signals over the bus means including inhibiting flow of digital signals over the bus means during that portion of an operational cycle during which ultrasonic waves are generated and analyzed, and transmitting digital signals over the bus means when the ultrasonic waves are not being generated and analyzed, wherein an ultrasonic portion of a test apparatus is effectively isolated from the bus means to prevent digital noise from effecting test information developed during the ultrasonic portion of the operational cycle.

11. The method of claim 10 further including changing the test parameters between one test cycle and another, the changing in test parameters being dynamically accomplished so that no down-time is required to change the test parameters between test cycles.

12. The method of claim 11 wherein changing the test parameters dynamically includes controlling the routing of digital signals over the bus such that digital signals for changing test parameters are allowed on the bus at the start of a test cycle and prior to the generation of ultrasonic waves.

13. A method for routing both analog and digital data signals from one location in a system to another including establishing a quiet bus having both analog and digital signals routed thereover, interfacing the quiet bus with control means which controls the flow of analog and digital signals thereover with the analog signals being routed between one set of locations within the system and the digital signals between a different set of locations therewithin, and controlling the flow of analog and digital signals by the control means such that the analog and digital signals rae not simultaneously present on the bus wherein digital noise associated with the presence of the digital signals cannot effect the signal characteristics of the analog signals.

14. The method of claim 13 wherein the routing of analog and digital data signals over the bus includes first allowing digital signals but not analog signals on the bus, then allowing analog signals but not digital signals on the bus, and then again allowing digital signals but not analog signals on the bus.

15. A quiet bus for use in routing analog and digital information in a using system from respective first locations in the system to respective second locations therewithin, the quiet bus having associated control means by which the routing of the information is controlled, the control means first allowing only digital information to be routed over the quiet bus, then only analog information over the quiet bus, and then again only digital information thereover, wherein analog and digital information is never simultaneously on the bus.

* * * * *

UNITED STATES PATENT AND TRADEMARK OFFICE
CERTIFICATE OF CORRECTION

PATENT NO. : 5,287,291
DATED : February 15, 1994
INVENTOR(S) : Cuffe, et al

It is certified that error appears in the above-indentified patent and that said Letters Patent is hereby corrected as shown below:

Column 1, line 16, after "test" insert therefor ---.---;

Column 8, line 68, delete "rae" and insert therefor ---are ---;

Signed and Sealed this

Sixteenth Day of August, 1994

Attest:

BRUCE LEHMAN

Attesting Officer     Commissioner of Patents and Trademarks